United States Patent
Ravid et al.

(10) Patent No.: US 11,259,715 B2
(45) Date of Patent: Mar. 1, 2022

(54) MONITORING AND DIAGNOSTICS SYSTEMS AND METHODS

(71) Applicant: ZOLL MEDICAL ISRAEL LTD., Kfar Sabba (IL)

(72) Inventors: Rafi Ravid, Savion (IL); Uriel Weinstein, Mazkeret Batya (IL); Roman Vaistikh, Ganei Tikva (IL); Gil Arditi, Binyamina (IL)

(73) Assignee: ZOLL MEDICAL ISRAEL LTD., Kfar-Saba (IL)

( * ) Notice: Subject to any disclaimer, the term of this patent is extended or adjusted under 35 U.S.C. 154(b) by 739 days.

(21) Appl. No.: 15/509,483

(22) PCT Filed: Sep. 8, 2015

(86) PCT No.: PCT/US2015/048971
§ 371 (c)(1),
(2) Date: Aug. 24, 2017

(87) PCT Pub. No.: WO2016/040337
PCT Pub. Date: Mar. 17, 2016

(65) Prior Publication Data
US 2017/0296093 A1    Oct. 19, 2017

Related U.S. Application Data

(60) Provisional application No. 62/047,534, filed on Sep. 8, 2014.

(51) Int. Cl.
*A61B 5/08*    (2006.01)
*A61B 5/021*   (2006.01)
(Continued)

(52) U.S. Cl.
CPC .......... *A61B 5/0809* (2013.01); *A61B 5/0215* (2013.01); *A61B 5/02125* (2013.01);
(Continued)

(58) Field of Classification Search
CPC ........ A61B 2563/0228; A61B 5/02125; A61B 5/0215; A61B 5/05; A61B 5/0809; A61B 5/0816
See application file for complete search history.

(56) References Cited

U.S. PATENT DOCUMENTS 4,240,445 A    12/1980    Iskander et al.
4,344,440 A     8/1982    Aaby et al.
(Continued)

FOREIGN PATENT DOCUMENTS

CN    101032400 A    9/2007
CN    101516437 A    8/2009
(Continued)

OTHER PUBLICATIONS

International Search Report and Written Opinion dated Dec. 10, 2015 for PCT/US2015/048971, filed Sep. 8, 2015.
(Continued)

*Primary Examiner* — Michael T Rozanski
(74) *Attorney, Agent, or Firm* — Cooley LLP

(57) ABSTRACT

Embodiments of the present disclosure provide methods, apparatuses, devices and systems for measuring vital signs in human and animals by interrogating electromagnetic signals reflected from tissues in a human or animal subject. Probes may transmit radio frequency electromagnetic waves into a living body and generate signals responsively to the waves that are scattered from within the body. Such embodiments may be suitable for wearable devices as well as for use by medical practitioners.

18 Claims, 9 Drawing Sheets

Examples of use cases corresponding to some embodiments of the Vital Signs Radar and Dielectrometer (VSRD) system to measure vital signs.

(51) Int. Cl.
*A61B 5/0215* (2006.01)
*A61B 5/05* (2021.01)

(52) U.S. Cl.
CPC .............. *A61B 5/05* (2013.01); *A61B 5/0816* (2013.01); *A61B 2562/0228* (2013.01)

(56) References Cited

U.S. PATENT DOCUMENTS

| | | |
|---|---|---|
| 4,557,272 A | 12/1985 | Carr |
| 4,632,128 A | 12/1986 | Paglione et al. |
| 4,640,280 A | 2/1987 | Sterzer |
| 4,641,659 A | 2/1987 | Sepponen |
| 4,774,961 A | 10/1988 | Carr |
| 4,825,880 A | 5/1989 | Stauffer et al. |
| 4,926,868 A | 5/1990 | Larsen |
| 4,945,914 A | 8/1990 | Allen |
| 4,958,638 A | 9/1990 | Sharpe |
| 4,986,870 A | 1/1991 | Frohlich |
| 5,003,622 A | 3/1991 | Ma et al. |
| 5,109,855 A | 5/1992 | Guner |
| 5,394,882 A | 3/1995 | Mawhinney |
| 5,404,877 A | 4/1995 | Nolan |
| 5,474,574 A | 12/1995 | Payne et al. |
| 5,540,727 A | 7/1996 | Tockman et al. |
| 5,549,650 A | 8/1996 | Bornzin et al. |
| 5,668,555 A | 9/1997 | Starr |
| 5,704,355 A | 1/1998 | Bridges |
| 5,766,208 A | 6/1998 | McEwan |
| 5,807,257 A | 9/1998 | Bridges |
| 5,829,437 A | 11/1998 | Bridges |
| 5,841,288 A | 11/1998 | Meaney et al. |
| 5,865,177 A | 2/1999 | Segawa |
| 5,967,986 A | 10/1999 | Cimochowski et al. |
| 6,019,724 A | 2/2000 | Gronningsaeter et al. |
| 6,025,803 A | 2/2000 | Bergen et al. |
| 6,061,589 A | 5/2000 | Bridges et al. |
| 6,064,903 A | 5/2000 | Riechers et al. |
| 6,093,141 A | 7/2000 | Mosseri et al. |
| 6,144,344 A | 11/2000 | Kim |
| 6,161,036 A | 12/2000 | Matsumara et al. |
| 6,193,669 B1 | 2/2001 | Degany et al. |
| 6,208,286 B1 | 3/2001 | Rostislavovich et al. |
| 6,233,479 B1 | 5/2001 | Haddad et al. |
| 6,267,723 B1 | 7/2001 | Matsumura et al. |
| 6,330,479 B1 | 12/2001 | Stauffer |
| 6,409,662 B1 | 6/2002 | Lloyd et al. |
| 6,454,711 B1 | 9/2002 | Haddad et al. |
| 6,471,655 B1 | 10/2002 | Baura |
| 6,480,733 B1 | 11/2002 | Turcott |
| 6,526,318 B1 | 2/2003 | Ansarinia |
| 6,592,518 B2 | 7/2003 | Denker et al. |
| 6,604,404 B2 | 8/2003 | Paltieli et al. |
| 6,729,336 B2 | 5/2004 | Da Silva et al. |
| 6,730,033 B2 | 5/2004 | Yao et al. |
| 6,755,856 B2 | 6/2004 | Fierens et al. |
| 6,933,811 B2 | 8/2005 | Enokihara et al. |
| 6,940,457 B2 | 9/2005 | Lee et al. |
| 7,020,508 B2 | 3/2006 | Stivoric et al. |
| 7,122,012 B2 | 10/2006 | Bouton et al. |
| 7,130,681 B2 | 10/2006 | Gebhardt et al. |
| 7,184,824 B2 | 2/2007 | Hashimshony |
| 7,191,000 B2 | 3/2007 | Zhu et al. |
| 7,197,356 B2 | 3/2007 | Carr |
| 7,266,407 B2 | 9/2007 | Li et al. |
| 7,267,651 B2 | 9/2007 | Nelson |
| 7,272,431 B2 | 9/2007 | McGrath |
| 7,280,863 B2 | 10/2007 | Shachar |
| 7,454,242 B2 | 11/2008 | Fear et al. |
| 7,474,918 B2 | 1/2009 | Frants et al. |
| 7,479,790 B2 | 1/2009 | Choi |
| 7,493,154 B2 | 2/2009 | Bonner et al. |
| 7,529,398 B2 | 5/2009 | Zwirn et al. |
| 7,570,063 B2 | 8/2009 | Van Veen et al. |
| 7,591,792 B2 | 9/2009 | Bouton |
| 7,697,972 B2 | 4/2010 | Verard et al. |
| 7,719,280 B2 | 5/2010 | Lagae et al. |
| 7,747,302 B2 | 6/2010 | Milledge et al. |
| 7,868,627 B2 | 1/2011 | Turkovskyi |
| 8,032,211 B2 | 10/2011 | Hashimshony et al. |
| 8,211,040 B2 | 7/2012 | Kojima et al. |
| 8,295,920 B2 | 10/2012 | Bouton et al. |
| 8,352,015 B2 | 1/2013 | Bernstein et al. |
| 8,473,054 B2 | 6/2013 | Pillai et al. |
| 8,682,399 B2 | 3/2014 | Rabu |
| 8,882,759 B2 | 11/2014 | Manley et al. |
| 8,938,292 B2 | 1/2015 | Hettrick et al. |
| 8,983,592 B2 | 3/2015 | Belalcazar |
| 8,989,837 B2 | 3/2015 | Weinstein et al. |
| 9,220,420 B2 | 12/2015 | Weinstein et al. |
| 9,265,438 B2 | 2/2016 | Weinstein et al. |
| 9,572,512 B2 | 2/2017 | Weinstein et al. |
| 9,629,561 B2 | 4/2017 | Weinstein et al. |
| 9,788,752 B2 | 10/2017 | Weinstein et al. |
| 10,136,833 B2 | 11/2018 | Weinstein et al. |
| 10,548,485 B2 | 2/2020 | Arditi et al. |
| 10,561,336 B2 | 2/2020 | Rappaport et al. |
| 10,588,599 B2 | 3/2020 | Weinstein et al. |
| 10,660,609 B2 | 5/2020 | Weinstein et al. |
| 10,680,324 B2 | 6/2020 | Weinstein et al. |
| 11,013,420 B2 | 5/2021 | Ravid et al. |
| 11,020,002 B2 | 6/2021 | Weinstein et al. |
| 11,108,153 B2 | 8/2021 | Weinstein et al. |
| 2002/0032386 A1 | 3/2002 | Sackner et al. |
| 2002/0045836 A1 | 4/2002 | Alkawwas |
| 2002/0049394 A1 | 4/2002 | Roy et al. |
| 2002/0050954 A1 | 5/2002 | Jeong-Kun et al. |
| 2002/0147405 A1 | 10/2002 | Denker et al. |
| 2002/0151816 A1 | 10/2002 | Rich et al. |
| 2003/0036674 A1 | 2/2003 | Bouton |
| 2003/0036713 A1 | 2/2003 | Bouton et al. |
| 2003/0088180 A1 | 5/2003 | Van Veen et al. |
| 2003/0100815 A1 | 5/2003 | Da Silva et al. |
| 2003/0199770 A1 | 10/2003 | Chen et al. |
| 2003/0219598 A1 | 11/2003 | Sakurai |
| 2004/0015087 A1 | 1/2004 | Boric-Lubecke et al. |
| 2004/0073081 A1 | 4/2004 | Schramm |
| 2004/0077943 A1 | 4/2004 | Meaney et al. |
| 2004/0077952 A1 | 4/2004 | Rafter et al. |
| 2004/0249257 A1 | 12/2004 | Tupin et al. |
| 2004/0254457 A1 | 12/2004 | van der Weide |
| 2004/0261721 A1 | 12/2004 | Steger |
| 2005/0038503 A1 | 2/2005 | Greenhalgh et al. |
| 2005/0107693 A1 | 5/2005 | Fear et al. |
| 2005/0192488 A1 | 9/2005 | Bryenton |
| 2005/0245816 A1 | 11/2005 | Candidus et al. |
| 2006/0004269 A9 | 1/2006 | Caduff et al. |
| 2006/0009813 A1 | 1/2006 | Taylor et al. |
| 2006/0025661 A1 | 2/2006 | Sweeney et al. |
| 2006/0101917 A1 | 5/2006 | Merkel |
| 2006/0237223 A1 | 10/2006 | Chen et al. |
| 2006/0265034 A1 | 11/2006 | Aknine et al. |
| 2007/0016032 A1 | 1/2007 | Aknine |
| 2007/0016050 A1 | 1/2007 | Moehring et al. |
| 2007/0055123 A1 | 3/2007 | Takiguchi |
| 2007/0100385 A1 | 5/2007 | Rawat |
| 2007/0123770 A1 | 5/2007 | Bouton et al. |
| 2007/0123778 A1 | 5/2007 | Kantorovich |
| 2007/0135721 A1 | 6/2007 | Zdeblick |
| 2007/0152812 A1 | 7/2007 | Wong et al. |
| 2007/0156057 A1 | 7/2007 | Cho et al. |
| 2007/0162090 A1 | 7/2007 | Penner |
| 2007/0191733 A1 | 8/2007 | Gianchandani et al. |
| 2007/0263907 A1 | 11/2007 | McMakin et al. |
| 2008/0027313 A1 | 1/2008 | Shachar |
| 2008/0030284 A1 | 2/2008 | Tanaka et al. |
| 2008/0036668 A1 | 2/2008 | White et al. |
| 2008/0097199 A1 | 4/2008 | Mullen |
| 2008/0129511 A1 | 6/2008 | Yuen et al. |
| 2008/0139934 A1 | 6/2008 | McMorrow et al. |
| 2008/0167566 A1 | 7/2008 | Kamil et al. |
| 2008/0169961 A1 | 7/2008 | Steinway et al. |
| 2008/0183247 A1 | 7/2008 | Harding |
| 2008/0200802 A1 | 8/2008 | Bahavaraju et al. |
| 2008/0224688 A1 | 9/2008 | Rubinsky et al. |

(56) References Cited

U.S. PATENT DOCUMENTS

| | | |
|---|---|---|
| 2008/0269589 A1 | 10/2008 | Thijs et al. |
| 2008/0283282 A1 | 11/2008 | Kawasaki et al. |
| 2008/0294036 A1 | 11/2008 | Hoi et al. |
| 2008/0316124 A1 | 12/2008 | Hook |
| 2008/0319301 A1 | 12/2008 | Busse |
| 2009/0021720 A1 | 1/2009 | Hecker |
| 2009/0048500 A1 | 2/2009 | Corn |
| 2009/0076350 A1 | 3/2009 | Bly et al. |
| 2009/0153412 A1 | 6/2009 | Chiang et al. |
| 2009/0153433 A1 | 6/2009 | Nagai et al. |
| 2009/0187109 A1 | 7/2009 | Hashimshony |
| 2009/0203972 A1 | 8/2009 | Heneghan et al. |
| 2009/0227882 A1 | 9/2009 | Foo |
| 2009/0240132 A1 | 9/2009 | Friedman |
| 2009/0240133 A1 | 9/2009 | Friedman |
| 2009/0248450 A1 | 10/2009 | Fernandez |
| 2009/0262028 A1 | 10/2009 | Mumbru et al. |
| 2009/0281412 A1 | 11/2009 | Boyden et al. |
| 2009/0299175 A1 | 12/2009 | Bernstein et al. |
| 2009/0312615 A1 | 12/2009 | Caduff et al. |
| 2009/0322636 A1 | 12/2009 | Brigham et al. |
| 2010/0004517 A1 | 1/2010 | Bryenton |
| 2010/0013318 A1 | 1/2010 | Iguchi et al. |
| 2010/0052992 A1 | 3/2010 | Okamura et al. |
| 2010/0056907 A1 | 3/2010 | Rappaport et al. |
| 2010/0076315 A1 | 3/2010 | Erkamp et al. |
| 2010/0081895 A1 | 4/2010 | Zand |
| 2010/0106223 A1 | 4/2010 | Grevious |
| 2010/0152600 A1 | 6/2010 | Droitcour et al. |
| 2010/0256462 A1 | 10/2010 | Rappaport et al. |
| 2010/0265159 A1 | 10/2010 | Ando et al. |
| 2010/0305460 A1 | 12/2010 | Pinter et al. |
| 2010/0312301 A1 | 12/2010 | Stahmann |
| 2010/0321253 A1 | 12/2010 | Ayala Vazquez et al. |
| 2010/0332173 A1 | 12/2010 | Watson et al. |
| 2011/0004076 A1 | 1/2011 | Janna et al. |
| 2011/0009754 A1 | 1/2011 | Wenzel et al. |
| 2011/0022325 A1 | 1/2011 | Craddock et al. |
| 2011/0040176 A1 | 2/2011 | Razansky et al. |
| 2011/0060215 A1 | 3/2011 | Tupin et al. |
| 2011/0068995 A1 | 3/2011 | Baliarda et al. |
| 2011/0125207 A1 | 5/2011 | Nabutovsky et al. |
| 2011/0130800 A1 | 6/2011 | Weinstein et al. |
| 2011/0257555 A1 | 10/2011 | Banet et al. |
| 2012/0029323 A1 | 2/2012 | Zhao |
| 2012/0065514 A1 | 3/2012 | Naghavi et al. |
| 2012/0068906 A1 | 3/2012 | Asher et al. |
| 2012/0098706 A1 | 4/2012 | Lin et al. |
| 2012/0104103 A1 | 5/2012 | Manzi |
| 2012/0330151 A1 | 12/2012 | Weinstein et al. |
| 2013/0041268 A1 | 2/2013 | Rimoldi et al. |
| 2013/0053671 A1 | 2/2013 | Farra |
| 2013/0069780 A1 | 3/2013 | Tran et al. |
| 2013/0090566 A1 | 4/2013 | Muhlsteff et al. |
| 2013/0123614 A1 | 5/2013 | Bernstein et al. |
| 2013/0184573 A1 | 7/2013 | Pahlevan et al. |
| 2013/0190646 A1 | 7/2013 | Weinstein et al. |
| 2013/0225989 A1 | 8/2013 | Saroka et al. |
| 2013/0231550 A1 | 9/2013 | Weinstein et al. |
| 2013/0281800 A1 | 10/2013 | Saroka et al. |
| 2013/0297344 A1 | 11/2013 | Cosentino et al. |
| 2013/0310700 A1 | 11/2013 | Wiard et al. |
| 2014/0046690 A1 | 2/2014 | Gunderson et al. |
| 2014/0081159 A1 | 3/2014 | Tao et al. |
| 2014/0128032 A1 | 5/2014 | Muthukumar |
| 2014/0163425 A1 | 6/2014 | Tran |
| 2014/0288436 A1 | 9/2014 | Venkatraman et al. |
| 2015/0025333 A1* | 1/2015 | Weinstein ......... A61B 5/02158 600/301 |
| 2015/0150477 A1 | 6/2015 | Weinstein et al. |
| 2015/0164349 A1 | 6/2015 | Gopalakrishnan et al. |
| 2015/0335310 A1 | 11/2015 | Bernstein et al. |
| 2016/0073924 A1 | 3/2016 | Weinstein et al. |
| 2016/0095534 A1 | 4/2016 | Thakur |
| 2016/0198957 A1 | 7/2016 | Arditi et al. |
| 2016/0198976 A1 | 7/2016 | Weinstein et al. |
| 2016/0213321 A1 | 7/2016 | Weinstein et al. |
| 2016/0317054 A1 | 11/2016 | Weinstein et al. |
| 2016/0345845 A1 | 12/2016 | Ravid et al. |
| 2017/0035327 A1 | 2/2017 | Yuen et al. |
| 2017/0135598 A1 | 5/2017 | Weinstein et al. |
| 2017/0238966 A1 | 8/2017 | Weinstein et al. |
| 2019/0046038 A1 | 2/2019 | Weinstein et al. |
| 2019/0298208 A1 | 10/2019 | Weinstein et al. |
| 2020/0113447 A1 | 4/2020 | Arditi et al. |
| 2020/0297309 A1 | 9/2020 | Weinstein et al. |
| 2020/0381819 A1 | 12/2020 | Weinstein et al. |
| 2021/0244282 A1 | 8/2021 | Weinstein et al. |
| 2021/0251507 A1 | 8/2021 | Ravid et al. |

FOREIGN PATENT DOCUMENTS

| | | |
|---|---|---|
| DE | 10008886 | 9/2001 |
| EP | 1834588 A1 | 9/2007 |
| EP | 2506917 A1 | 10/2012 |
| EP | 2 602 870 A1 | 6/2013 |
| JP | 05-038957 | 5/1993 |
| JP | 10-137193 A | 5/1998 |
| JP | 2000-235006 A | 8/2000 |
| JP | 2001-525925 A | 12/2001 |
| JP | 2002-094321 | 3/2002 |
| JP | 2003-141466 | 5/2003 |
| JP | 2004-526488 A | 9/2004 |
| JP | 2006-208070 A | 8/2006 |
| JP | 2006-319767 A | 11/2006 |
| JP | 2007-061359 A | 3/2007 |
| JP | 2007-149959 | 6/2007 |
| JP | 2008-515548 A | 5/2008 |
| JP | 2008-148141 A | 6/2008 |
| JP | 2008-518706 A | 6/2008 |
| JP | 2008-530546 A | 7/2008 |
| JP | 2008-542759 A | 11/2008 |
| JP | 2008-545471 | 12/2008 |
| JP | 2009-514619 A | 4/2009 |
| JP | 2009-522034 A | 6/2009 |
| JP | 2010-507929 | 3/2010 |
| JP | 2010-072957 | 4/2010 |
| JP | 2010-512190 A | 4/2010 |
| JP | 2010-530769 | 9/2010 |
| JP | 2010-537766 A | 12/2010 |
| JP | 2011-507583 | 3/2011 |
| JP | 2011-524213 A | 9/2011 |
| JP | 2012-090257 | 5/2012 |
| WO | WO 02/03499 A1 | 1/2002 |
| WO | WO 2003/009752 A2 | 2/2003 |
| WO | WO 2006/127719 A2 | 11/2006 |
| WO | WO 2006/130798 A2 | 12/2006 |
| WO | WO 2007/017861 A2 | 2/2007 |
| WO | WO 2007/023426 A2 | 3/2007 |
| WO | WO 2008/070856 A2 | 6/2008 |
| WO | WO 2008/148040 A1 | 12/2008 |
| WO | WO 2009/031149 A2 | 3/2009 |
| WO | WO 2009/031150 A2 | 3/2009 |
| WO | WO 2009/060182 A1 | 5/2009 |
| WO | WO 2009/081331 A1 | 7/2009 |
| WO | WO 2009/152625 A1 | 12/2009 |
| WO | WO 2011/067623 A1 | 6/2011 |
| WO | WO 2011/067685 A1 | 6/2011 |
| WO | WO 2011/141915 A2 | 11/2011 |
| WO | WO 2012/011065 A1 | 1/2012 |
| WO | WO 2012/011066 A1 | 1/2012 |
| WO | WO 2013/118121 A1 | 8/2013 |
| WO | WO 2013/121290 A2 | 8/2013 |
| WO | WO 2015/118544 A1 | 8/2015 |
| WO | WO 2016/040337 A1 | 3/2016 |

OTHER PUBLICATIONS

Alekseev, S. I., et al. "Human Skin permittivity determined by millimeter wave reflection measurements", Bioelectromagnetics, vol. 28, No. 5, Jul. 1, 2007, pp. 331-339.

(56) References Cited

OTHER PUBLICATIONS

Ascension Technology Corporation, "TrakSTAR Adds Versatility to Ascension's New Product Line: Desktop Model Joins driveBAY Tracker for Fast Guidance of Miniaturized Sensor", USA, Apr. 7, 2008.

Bell et al., "A Low-Profile Achimedean Spiral Antenna Using an EBG Ground Plane", IEEE Antennas and Wireless Propagation Letters 3, pp. 223-226 (2004).

Beyer-Enke et al., Intra-arterial Doppler flowmetry in the superficial femoral artery following angioplasty., 2000, European Radiology, vol. 10, No. 4, p. 642-649.

Claron Technology Inc., "MicronTracker 3:A New Generation of Optical Trackers", Canada, 2009.

Czum et al., "The Vascular Diagnostic Laboratory", The Heart & Vascular Institute Newsletter, vol. 1, USA, Winter, 2001.

Ghosh, et al., Immediate Evaluation of Angioplasty and Stenting Results in Supra-Aortic Arteries by Use of a Doppler-Tipped Guidewire, Aug. 2004, American Journal of Neuroradiology, vol. 25, p. 1172-1176.

Gentili et al., "A Versatile Microwave Plethysmograph for the Monitoring of Physiological Parameters", IEEE Transactions on Biomedical Engineering, IEEE Service Center, Pitscataway, NJ, US, vol. 49, No. 10, Oct. 1, 2002.

Haude et al., Intracoronary Doppler-and Quantitative Coronary Angiography-Derived Predictors of Major Adverse Cardiac Events After Stent Implantation, Mar. 6, 2001, Circulation, vol. 103(9), p. 1212-1217.

Immersion Corporation, "Immersion Introduces New 3D Digitizing Product-MicroScribe G2; Faster Data Transfer, USB Compatibility, New Industrial Design", Press Release, San Jose, USA, Jul. 1, 2002.

Kantarci et al., Follow-Up of Extracranial Vertebral Artery Stents with Doppler Sonography., Sep. 2006, American Journal of Roentgenology, vol. 187, p. 779-787.

Lal et al., "Duplex ultrasound velocity criteria for the stented carotid artery", Journal of Vascular Surgery, vol. 47, No. 1, pp. 63-73, Jan. 2008.

Larsson et al., "State Diagrams of the Heart—a New Approach to Describing Cardiac Mechanics", Cardiovascular Ultrasound 7:22 (2009).

Liang, Jing et al., Microstrip Patch Antennas on Tunable Electromagnetic Band-Gap Substrates, IEEE Transactions on Antennas and Propagation, vol. 57, No. 6, Jun. 2009.

Lin, J.C. et al., "Microwave Imaging of Cerebral Edema", Proceedings of the IEEE, IEEE, NY, US, vol. 70, No. 5; May 1, 1982, pp. 523-524.

Lin et al.: "Using dual-antenna nanosecond pulse near field sensing technology for non-contact and continuous blood pressure measurement", Engineering in Medicine and Biology Society (EMBC), 2013 35th Annual International Conference of the IEEE, IEEE, Aug. 28, 2012 (Aug. 28, 2012), pp. 219-222.

Miura et al. "Time Domain Reflectometry: Measurement of Free Water in Normal Lung and Pulmonary Edema," American Journal of Physiology—Lung Physiology 276:1 (1999), pp. L207-L212.

Paulson, Christine N., et al. "Ultra-wideband radar methods and techniques of medical sensing and imaging" Proceedings of Spie, vol. 6007, Nov. 9, 2005, p. 60070L.

Pedersen, P. C., et al., "Microwave Reflection and Transmission Measurements for Pulmonary Diagnosis and Monitoring", IEEE Transactions on Biomedical Engineering, IEEE Service Center, Piscataway, NJ, US, vol. BME-19, No. 1, Jan. 1, 1978; pp. 40-48.

Polhemus, "Fastrak: The Fast and Easy Digital Tracker", USA, 2008.

Ringer et al., Follow-up of Stented Carotid Arteries by Doppler Ultrasound, Sep. 2002, Neurosurgery, vol. 51, No. 3, p. 639-643.

Solberg et al: "A feasibility study on aortic pressure estimation using UWB radar", Ultra-Wideband, 2009. ICUWB 2009. IEEE International Conference on, IEEE, Piscataway, NJ, USA, Sep. 9, 2009 (Sep. 9, 2009), pp. 464-468.

Yang, F. et al. "Enhancement of Printed Dipole Antennas Characteristics Using Semi-EBG Ground Plane", Journal of Electromagnetic Waves and Application, U.S., Taylor & Francis, Apr. 3, 2006, vol. 8, pp. 993-1006.

Lin et al., "Enhanced performances of a compact conical pattern annular-ring patch antenna using a slotted ground plane," Microwave Conference, 2001. APMC 2001. 2001 Asia-Pacific Dec. 3-6, 201, IEEE, vol. 3, Dec. 3, 2001, pp. 1036-1039.

Matsugatani et al., "Surface Wave Distribution Over Electromagnetic Bandgap (EBG) And EBG Reflective Shield For Patch Antenna," IEICE Transactions On Electronics, vol. E88-C, No. 12, Dec. 1, 2005, pp. 2341-2349.

Yang et al., "Reflection phase characterizations of the EBG ground plane for low profile wire antenna applications," IEEE Transactions on Antennas and Propagation, vol. 51, No. 10, Oct. 1, 2003, pp. 2691-2703.

Zhang et al., "Planar artificial magnetic conductors and patch antennas," IEEE Transactions on Antennasand Propagation, vol. 51, No. 10, Oct. 1, 2003, pp. 2704-2712.

\* cited by examiner

Figure 1 Examples of use cases corresponding to some embodiments of the Vital Signs Radar and Dielectrometer (VSRD) system to measure vital signs.

Figure 2. An example of the electrical components comprised in one embodiment of the VSRD sensor.

Figure 3. Example embodiments of the VSRD sensors, and a human and an animal subject wearing the sensor.

Example of steps to perform a heart rate calculation in one embodiment of the VSRD.

Examples of measurements taken with the VSDR sensor: blood pulse wave (shown next to an electrocardiogram for reference).

Example signal obtained by the VSRD sensor showing the pulse pressure based on systolic and diastolic blood pressure points.

Example method performed by the VSDR system process to calculate a subject's heart rate.

MONITORING AND DIAGNOSTICS SYSTEMS AND METHODS

CROSS-REFERENCE TO RELATED APPLICATIONS

This application is a National Phase of PCT Patent Application No. PCT/US2015/048971 having International filing date of Sep. 8, 2015, which claims priority under 35 USC § 119(e) to U.S. Provisional Patent Application Ser. No. 62/047,534 filed Sep. 8, 2014. The disclosures of which are herein incorporated by reference in their entirety.

FIELD OF THE DISCLOSURE

Radio-frequency (RF) electromagnetic radiation has been used for diagnostics and imaging purposes of body tissues. For example, RF electromagnetic waves may be transmitted into a living body and generate signals responsively to the waves that are scattered from within the body. Analysis of the received signals allow for the monitoring of the various tissues within the living body.

SUMMARY OF SOME OF THE EMBODIMENTS

Embodiments of the present disclosure provide methods, apparatuses, devices and systems for measuring vital signs of a subject, comprising a probe, at least one circuit and a processor having computer instructions operating thereon. In some embodiments, the probe is configured to be placed on or adjacent to skin of a subject, and generate one or more first radio-frequency (RF) waves for transmission towards a tissue and receive reflected RF waves therefrom. In some embodiments, the at least one circuit is configured to cause the probe to generate the first RF waves, and generate at least one signal corresponding to one or more of the reflected RF waves received by the probe. In some embodiments, the one or more first RF waves include one or more first characteristics, the one or more reflected RF waves include one or more second characteristics and the at least one signal includes information corresponding to at least one of the one or more second characteristics. Further, in some embodiments, the computer instructions are configured to cause the processor to determine at least one vital sign of the subject based upon one or more of the second characteristics and/or the difference between one or more of the second characteristics and one or more of the first characteristics of one or more of the reflected RF waves.

In some embodiments, the probe can comprise a monostatic radar, a bistatic radar, and/or a dielectrometer comprising a first conductor and a second conductor. The probe may be configured with flexibility for conforming the probe to the skin of the subject, and may also be configured to be placed on or adjacent to the skin of the subject via a wearable device or garment or an adhesive, or, an implantable device configured to be placed in proximity to the tissue. In some embodiments, the wearable garment comprises at least one of an article of clothing, a collar, a wrist strap, an ear tag, and a skin patch.

In some embodiments, the one or more first RF waves comprise stepped-frequency RF waves, continuous-frequency RF wave, and/or the like. Further, the at least one circuit is configured to cause the probe to generate the first RF waves and to receive the reflected RF wave at a plurality of frequencies, wherein the plurality of frequencies can range from about 200 MHz to about 3 GHz.

In some embodiments, the processor's computer instructions are further configured to cause the processor to resolve the at least one signal and/or the received reflected RF waves according to one or more depths into the subject from which one or more of the reflected RF waves occurred. Further, the computer instructions are configured to cause the processor to condition the at least one signal and/or the received, reflected RF waves using band pass filtering. In some embodiments, the probe may be placed in proximity to an artery, and the computer instructions are further configured to cause the processor to determine a time rate of occurrence of prominent peaks in a pulse waveform of the at least one signal and/or the received, reflected RF waves, and wherein the time rate corresponds to a heart rate of the subject. In such embodiments, the computer instructions can also be configured to cause the processor to identify a prominent peak frequency in a frequency range relevant to heartbeats of the subject from a power spectrum density of the at least one signal and/or the received, reflected RF waves. For example, the frequency range for the at least one signal and/or one or more first RF waves may correspond to between 0.5 Hz to 2.5 Hz. In some embodiments, the computer instructions are further configured to cause the processor to determine a heart rate of the subject as a function of the peak frequency.

In some embodiments, the probe can be placed at least in proximity to a torso of the subject, and the computer instructions are further configured to cause the processor to identify a prominent peak frequency in a frequency range of the received, reflected RF waves corresponding to respirations of the subject from a fast Fourier transform of the returned signal. For example, the frequency range can be between 0.1 Hz to 1 Hz. In some embodiments, the computer instructions are further configured to cause the processor to determine a respiration rate of the subject as a function of the peak frequency.

In some embodiments, the probe can be placed at least in proximity to a torso of the subject, and the computer instructions can be further configured to cause the processor to identify a prominent peak frequency in a frequency range of the received, reflected RF waves corresponding to respirations of the subject from a fast Fourier transform of the returned signal. For example, the frequency range can be between 0.1 Hz to 1 Hz. In some embodiments, the computer instructions are further configured to cause the processor to determine a respiration rate of the subject as a function of the peak frequency.

In some embodiments, the at least one signal and/or the received, reflected RF waves correspond to reflections from at least two different arterial tree locations of arteries of the subject, and the computer instructions can be further configured to cause the processor to: determine an arterial-pulse-arrival-time (PAT) at each of the two different arterial tree locations, and calculate a difference between the PAT at the two locations so as to determine an arterial-pulse-travel-time (PTT). In some embodiments, the at least one signal and/or the received, reflected one or more RF waves correspond to form at least two different arterial tree locations of arteries of the subject, and the computer instructions are further configured to cause the processor to: determine arterial-pulse-arrival-time (PAT) at each of the two different arterial tree locations, and calculate a difference between the PAT at the two locations so as to determine an arterial-pulse-travel-time (PTT). In some embodiments, the probe comprises a first sensor and a second sensor, the first sensor configured for receiving a first reflected RF wave from a first arterial tree location and the second sensor configured for receiving a second reflected RF wave from a second arterial tree location, the computer instructions are further configured to cause the processor to determine arterial-pulse-arrival-time (PAT) at each location, and calculate a difference between the PAT at the two locations so as to determine an arterial-pulse-travel-time (PTT).

In any of the above embodiments, the two arterial tree locations may comprise different locations on same arterial tree, locations on different arterial trees on same area of the body of a patient, locations on arterial trees on different areas of the body of a patient, and/or the like. Further, the computer instructions can be configured to cause the processor to determine a blood pressure of the subject as a function of the PTT.

In some embodiments, the probe comprises a dielectrometer comprising a first conductor and a second conductor; and the computer instructions can be further configured to cause the processor to calculate a complex permittivity from the at least one signal and/or one or more of the received, reflected RF waves by measuring an impedance between the first conductor and the second conductor.

DETAILED DESCRIPTION OF SOME OF THE EMBODIMENTS

Figure 1:
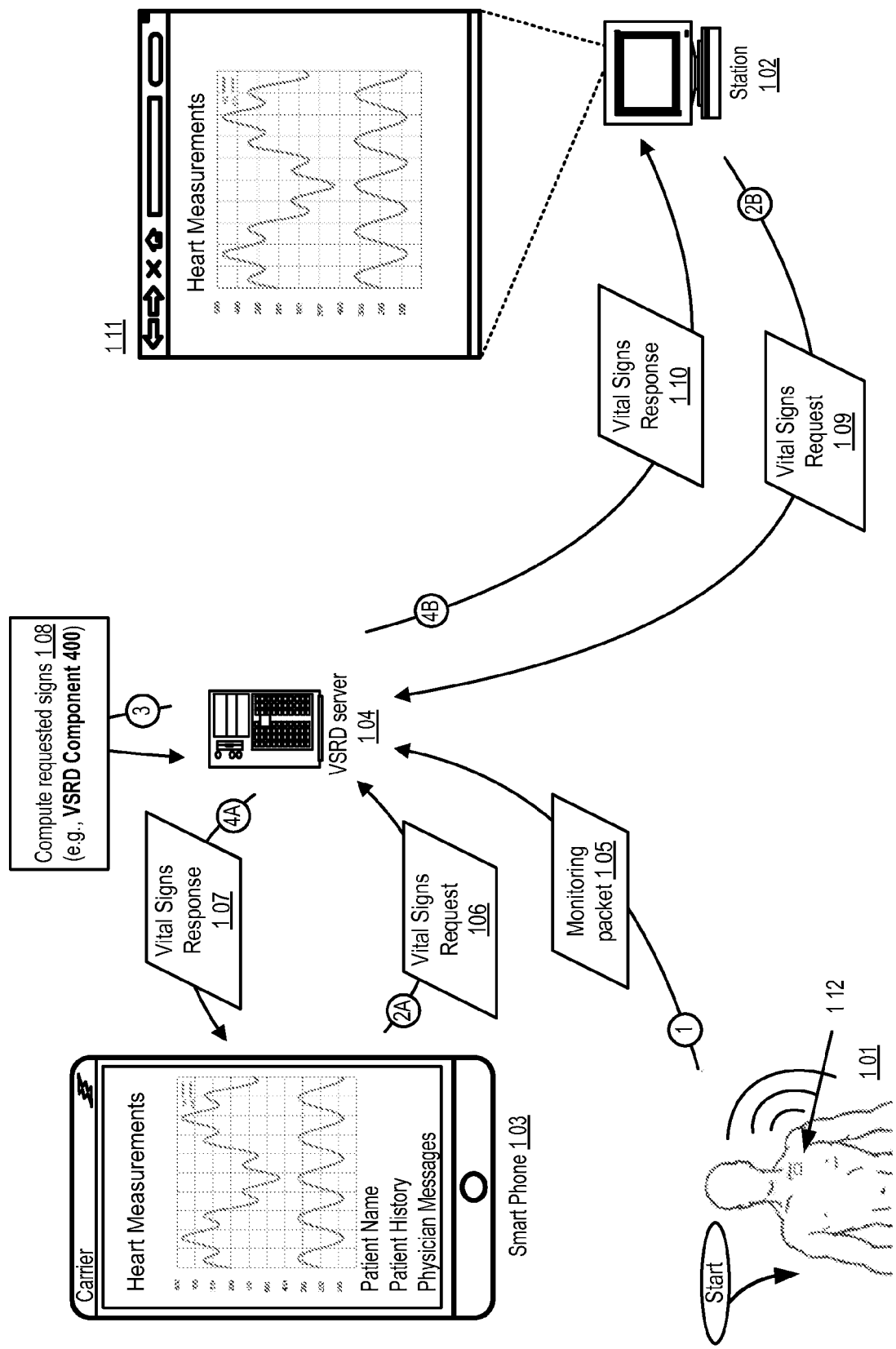
FIG. 1 shows examples of use cases corresponding to some embodiments of the Vital Signs Radar and Dielectrometer (VSRD) systems to measure vital signs, in one embodiment of the VSRD.

Embodiments of the present disclosure provide methods, apparatuses, devices and systems, for measuring humans and animals' vital signs utilizing a miniature medical RF sensor or transceiver and/or a dielectrometer. The vital signs of humans and animals alike that can be monitored include, but are not limited to, blood pressure, heart and respiration rates. Some of these embodiments may further include the monitoring of body temperature. For example, a temperature sensor incorporated in the apparatuses, devices and systems may be used to acquire a body temperature reading. In addition, the disclosed embodiments can provide means to detect muscle movements. In some instances, analysis of the monitored vital signs and/or the detected muscle movements may allow for the determination of the state, activity or behavior of the monitored animal or human. For example, by monitoring the muscle neck movements of cattle, one may determine that an animal is regurgitating. As another example, based on the vital signs readings (e.g., heart rate, body temperature, etc.) and/or muscle movement detection, embodiments of the present disclosure allow for determining the physical/physiological state of the animal or human body (e.g., active, stressed, fed, etc.).

Such embodiments of the present disclosure may be suitable for implementation as skin patches, ear tags, and/or may be integrated with wearable devices, embedded in clothing, mounted on a limb (e.g., wrist) or collar strap, and/or the like wearable embodiments. Other embodiments may comprise subcutaneous implements. In some embodiments, the apparatus or device is portable and is not physically tethered to other devices. Additionally, some embodiments may comprise an accelerometer or other movement sensor to determine the state of motion of the subject when a measurement is to be or being taken. For example, the device may be sensitive to motion, and the reliability of the measurements by the device may depend on the device's state of motion when the measurements are being taken. In some embodiments, an accelerometer (e.g., three-axial) may accompany the device, and the RF measurements may be calibrated based on the readings of the accelerometer (e.g., measurements may be conditioned or calibrated for low acceleration). In some embodiments, measurements may not take place or, if taken, the results may be discounted, if the readings show unacceptable state of motion (e.g., the measurements may not be accurate or reliable).

In some embodiments, the sensor is nonintrusive with respect to a subject and can read the subject's vital signs and other indications without requiring active intervention (from the subject or another), such vital signs and indications including heart rate, respiration rate, blood pressure, body temperature and/or RF-tonometry. Moreover, in some embodiments, the sensor can work directly over a subject's skin (e.g., with and without skin adhesives), clothing, fur and/or the like. The ease of use of the disclosed methods, apparatuses, devices and systems facilitates the monitoring of large numbers of subjects as is the case, for example, with livestock. For example, ear tags and neck collars comprising the disclosed RF sensor and/or dielectrometer can be used to measure the various physiological conditions and health state (e.g., vital signs, muscle movements, etc.) of large number of cattle, easing the difficulties presented when monitoring a large number of subjects.

In some of the embodiments of the present disclosure, apparatus, device and/or system configured to determine at least one of a subject's heart rate, respiration rate, blood pressure and body temperature are provided. In some embodiments, a sensor coupled to a subject's body may transmit radio frequency (RF) waves into the body tissue and receive reflected waves from the tissue. In one embodiment, the sensor can achieve range (depth) resolution allowing for the isolation of the reflections from the desired depth in the subject's body from other concurrent reflections or interferences. For example, based on an estimate of the depths of arteries and muscles in the line of sight of the transmitted and/or reflected signals, signals reflected from these tissues may be classified according to the reflecting tissue. For example, a frequency shift in the reflected signal can be used to determine the depths from which the reflections occurred, and knowledge of locations of tissues along the signal path leads to the identification of the tissue. As such, this resolution of the reflected signals allows for the proper identification of the tissue whose behavior is being monitored for determining vital signs and muscle activities of the subject body.

To determine the frequency shift of a reflected signal, in some embodiments, an analysis of the phase changes with respect to the transmitted signal may be performed. For example, a signal reflected from a distance d accrues a phase change proportional to the distance d compared to the transmitted signal, i.e., the transmitted signal's phase shifts to $e^{j\omega_i(t-2d/c)}$ compared to the transmitted signal's $e^{j\omega_i t}$. The change in the phase, $e^{-j\omega_i 2d/c}$, which can be obtained after down conversion with $e^{-j\omega_i t}$, can be interpreted as a frequency shift proportional to reflection distance d. Alternatively, the distance d can be determined based on the time of arrival of the signal after reflection. In some embodiments, a Fourier transform of the received signal may be performed to generate an image comprising frequency information of the reflected signal.

In some embodiments, the apparatus includes radar and/or a dielectrometric probe configured to transmitting signals of varied waveforms. For example, the radar and/or dielectrometric probe may transmit signals with continuous or stepped radio frequencies. In some embodiments, the radio frequencies can range from about 200 MHz to about 3 GHz, from about 200 MHz to about 300 MHz, from about 300 MHz to about 1 GHz, from about 1 GHz to about 2 GHz, from about 2 GHz to about 3 GHz, and/or the like. In some embodiments, a narrow band or a single frequency can be used for heart rate and respiration rate measurements. For example, a narrow band frequency range of from about 0.9 GHz to about 1 GHz, 1 GHz to about 1.1 GHz, 1.1 GHz to about 1.2 GHz, etc., and/or a single frequency of about 0.9 GHz, 1 GHz, 1.1 GHz, etc., can be used in monitoring heart and respiration rates of a human or animal subject.

In some embodiments, the sensor can be attached to a subject's body by a plurality of further embodiments, including but not limited to, skin patches enhanced with skin-friendly adhesive, pieces of clothing with the sensor embedded thereon (e.g., stockings, shirts, etc.), utilizing a wearable strap or collar, wrist based wears, an ear tag (e.g., for animals), a subcutaneous implant and/or the like embodiments. In some instances, the sensor may be configured with flexibility that allows the sensor to conform to the skin of the patient.

In some embodiments, when the sensor is attached to a subject's skin in proximity to an artery, the sensor can measure the subject's heart rate. In such embodiments, a plurality of reflected radar signals is received by the sensor modulated by the different tissue layers, positioned at different depths within the body. For example, the radar signals may be in the form of stepped-frequency. These signals can be filtered to isolate the signal corresponding to a subject's prominent artery thus, detecting the artery's modulation. For example, by estimating the depth of the different tissue layers (arteries, muscles, etc.), the signals reflected by a respective tissue layer may be identified. Upon the identification of reflected signals according to the reflecting tissue layer, the reflected signals may be analyzed to determine properties or behaviors of the tissue layers. For example, the sensor can analyze changes in amplitude from isolated signal reflected from an artery to determine the arterial pulse wave and thenceforth calculate the subject's heart rate, blood pressure, and/or the like. For example, the rate of the prominent peaks appearing in the signal waveforms can be used to calculate the heart rate. In some embodiments, "prominent peaks" refer to amplitude values in the signal waveform that exceed other nearby amplitude values (as a function of time, frequency, etc.).

In some embodiments, RF signal reflected from within a subject's body may be analyzed to determine the depths from which the signals are reflected from. For example, depths of tissues such as arteries, muscles, etc., may be estimated and a determination may be made as to which tissue a reflected signal came from. In this manner, changes in the reflected signal (for example, as they relate to the transmitted signal) may be analyzed to identify properties and/or behaviors of the reflecting tissue. For example, one may estimate the depth of an artery, and identify or isolate the RF signal whose reflection depth at least substantially matches the depth of the artery. This reflected wave then may be analyzed to obtain the arterial pulse waveform of the reflecting artery. For example, the signal may be filtered to enhance signal quality, examples of such filtering including low pass filtering to remove noise artifacts. In some embodiments, one may identify some or all prominent peaks in the filtered or unfiltered signals and estimate the rate of the peaks. For example, the time separation between peaks may at least substantially correspond to the period (e.g., average) of the heart rate of the subject being monitored. Alternatively, or in conjunction, in some embodiments, one may calculate the power spectrum density (PSD) of the signal and estimate from the PSD the frequency of the prominent peaks in the frequency range relevant to the heart rate, which one may then ascribe to the heart rate.

In some embodiments, when the sensor is attached to a subject's torso, the reflected signals can be modulated by a respiration cycle of the subject, i.e., the reflected signal may contain signatures of the subject's respiration, including the respiration rate. An analysis of the reflected signal can then isolate the frequency of the respiration. For example, the sensor can calculate the subject's respiration rate form the sensor signals by collecting the reflected signals received by the sensor, and performing a fast Fourier transformation (FFT) to the signals to determine the peak frequencies in the FFT signals. In some embodiments, one may identify a peak frequency in the respiration frequency range relevant to respirations of subjects as the respiration rate of the subject. The frequency range may depend on a variety of factors such as the subject's state (e.g., active vs. passive), etc. In any case, the range may be estimated and a peak in the range can then be ascribed to the respiration rate.

In some embodiments, a subject's blood pressure can be calculated from the arterial's pulse waveform detected by the sensor. For example, the sensor can estimate the depth of a prominent artery and utilize the received reflected signals substantially corresponding to such depth to obtain a signal corresponding to the arterial pulse waveform. In some embodiments, the reflected signals are modulated by the artery as it changes its radar cross section (RCS). In some embodiments, the pulse waveform signal can be substantially identical to a tonometry signal. For example, the systolic and diastolic blood pressures can be determined by assigning the maximum value of the pulse waveform and the minimum value of the pulse waveform respectively to each pressure measurement.

In some embodiments, a plurality of sensors may be used to determine blood pressure measurements. For example, a pair of RF sensors may be located over two respective arteries along an arterial tree, and the time difference between pulse wave arrivals at the two locations may be measured by the sensors. The pulse wave velocity (PWV), corresponding to the velocity of propagation of the arterial pressure pulse between points along the arterial tree, and/or the pulse transit time (PTT), corresponding to the transit time, may be determined from the measurements of the sensors. The PWV and/or the PTT can be related to the blood pressure, and as such, the blood pressure may be determined from these measurements. For example, changes in the PTT can be correlated to blood pressure changes. The determination of blood pressure measurements using electromagnetic waves is discussed in PCT Publication No. WO/2015/118544, incorporated herein by reference in its entirety.

In some embodiments, the PTT at some point along the arterial tree (e.g., peripheral location in the arterial system) may be represented as the difference between the arrival time of the pulse at the point, the pulse arrival time (PAT), and the pre-ejection period (PEP), i.e., PTT=PAT−PEP. The PEP can be the lapse between the ventricular polarization and the opening of the aortic valve, which corresponds to the time it takes for the myocardium to raise sufficient pressure to open the aortic valve and start pushing blood out of the ventricle. Upon determining or estimating the PTT, in some embodiments, the PWV may then be calculated based on the distance the pulse traveled to arrive at the point and the estimated/determined PTT. In some implementations, blood pressure values such as systolic and/or diastolic values can be determined non-invasively from the PWV and/or the PTT. For example, linear transformations relating the systolic blood pressure (SBP) and diastolic blood pressure (DBP) to the PTT may be expressed as follow:

$$SBP=(a \times PTT)+b,$$

$$DBP=(c \times PTT)+d,$$

where the coefficients a, b, c and d can be calibrated for each patient. In some embodiments, other types of transformations may be used to calculate blood pressures. For example, for a model that assumes constant artery thickness and radius, blood pressure P may be expressed as P=a×ln(PTT)+b, where, again a and b are constants to be calibrated for each patient. In any case, in some embodiments, obtaining PTT, or conversely PWV of a pulse in an artery, may lead to the determination of blood pressure levels in the artery.

In some embodiments, the PTT of the pulse can be determined if the times of arrival of the pulse at two distinct locations can be measured. This follows because the PEP values of the pulse that originated at the same ventricle but arrived at the two different locations is the same, and accordingly, the difference in PAT for the two locations is the same as the difference in PTT of the pulse at the two distinct locations. For example, two RF sensors located at different locations on a body (e.g., the sternum and the thorax, two suitable locations along the leg, etc. of a human subject) can be used to sense the pulse wave going through arteries close to each RF sensor, and the difference in the times of arrival at the two locations can represent and be used to determine the PTT.

In some embodiments, the sensor comprises a dielectrometer probe configured to measure the dielectric properties of the tissue, and dielectrometer probe may be used in measuring the heart rate of a subject. For example, the dielectrometer can sense changes in the dielectric properties induced by the blood flow in an artery when a sensor is attached to a subject's skin in proximity to the artery. The measurement of the dielectric properties of physiological tissues is discussed in US/2013/0190646, incorporated herein by reference in its entirety.

In some embodiments, the sensor comprises a dielectrometric probe with a pair of conductors, which can be attached to a subject's skin in proximity to an artery. Thereafter, a driving circuit applies a radio-frequency signal to the probe and senses a signal returned from the probe in order to measure the impedance between the aforementioned conductors. The impedance varies as a function of the dielectric properties of the target tissue, e.g., the artery, including the relative permittivity, the conductivity and the loss or dissipation factor, which can be used to define the complex permittivity of the tissue. The driving circuit can apply the radio-frequency signal to the probe at a plurality of frequencies, so that the complex permittivity can be measured as a function of the frequency. A processing circuit may then evaluate the dielectric properties of the target tissue and calculate the impedance. Following the impedance calculation over frequency, an analysis of the signal can be carried out to estimate the heart rate, respiratory rate and arterial pulse waveform.

In a general material including loss and permittivity, impedance is defined as follows: $\eta=j\omega\mu/\gamma$. Here $\omega$ is the radial frequency, and $\mu$ is the material permeability (which in the case of a biological tissue can equal the free space permeability $\mu=\mu_0$). $\gamma$ is the complex propagation constant which can be defined as $\gamma=j\omega\sqrt{(\mu\varepsilon_0)}\sqrt{(\varepsilon'-j\varepsilon'')}$, wherein $\varepsilon'$ and $\varepsilon''$ are the real and imaginary parts of the complex permittivity, and the imaginary part of the complex permittivity is related to the conductivity via $\varepsilon''=\sigma/\omega\varepsilon_0$. In some embodiments, the above expressions are thus used to relate the measured impedance, as a function of frequency, to the complex permittivity.

The impedance between the conductors due to the target tissue can be measured in a number of ways. In some embodiments, the driving circuit measures the reflection of the signal from the probe, which is indicative of an impedance mismatch at the target tissue at the end of the probe. In other embodiments, the driving circuit measures the delay of the signal transmitted through the probe, which is indicative of the permittivity of the target tissue. In other embodiments, the driving circuit measures a resonating frequency of a printed resonator (such as a ring or other shaped circuit), which is indicative of the properties of tissues in its proximity.

Using a dielectrometer, in some embodiments, one may measure the dielectric properties of target tissues, and sample the output of the dielectrometer over time to obtain the time dependence of the dielectric property. For example, the time dependence of the permittivity of the target tissue $\varepsilon(t)$ may be determined from the sampled outputs of the dielectrometer. In some embodiments, $\varepsilon(t)$ may be low pass filtered to remove noises, and some or all prominent peaks of the permittivity may be detected. From the rate of the prominent peaks, in some embodiments, the heart rate of the subject to which the sensor comprising the dielectrometer is coupled may be determined.

In some embodiments, the above procedure may be repeated with a plurality of frequencies, and in such embodiments, the steps of i) sampling the dielectrometer output to determine $\varepsilon(t)$, ii) low-pass filtering the output/$\varepsilon(t)$ to remove noise, iii) detecting prominent peaks from the signals in the frequency range of interest, and iv) determining the rate of the prominent peaks in the desired range can be performed for each frequency, and those frequencies that at least closely correspond to the periodicity of the heart rate may be used in determining the heart rate of the subject.

In some embodiments, the sensor comprises means to calibrate the amplitude of a waveform using a reference blood measurement device. The systolic and diastolic blood pressures can be determined by assigning the maximum value of the calibrated pulse waveform and the minimum value of the calibrated pulse waveform respectively to each measurement.

In some embodiments, the Vital Signs Radar and Dielectrometer (VSRD) sensor 112 utilizes an embedded radar to calculate measures of vital signs such as but not limited to respiration rate, blood pressure, heart rate, and/or body temperature. Heart rate measurements can additionally or alternatively be measured with an embedded dielectrometer. Examples of use cases corresponding to some embodiments of the (VSRD) sensor to measure vital signs are shown in FIG. 1. In some embodiments, a patient 101 has a sensor attached to his chest in direct proximity to one of his arteries. The sensor 112 can continuously collect vital signs data and send it through a network access point to a VSRD server 104 via a monitoring packet e.g., 105. In some embodiments, the telemetry communications can be performed via Bluetooth, Wi-Fi, cellular and the like wireless interfaces. Thereafter, a request to view the subjects vital signs e.g., 106 and 109 can be received from a physician's or from the patient's mobile device e.g., smart phone 103. In another embodiment, the request to view the human or animal vital signs e.g., 106 and 109 can be received from a physician's or from the patient's computer station e.g., 102. After receiving a vital signs request e.g., 106 and 109, the VSRD server 107 computes the requested signs.

In some embodiments, the described telemetry can be performed according to a predetermined scheduled regime for example, once a week, day, hour and/or other predetermined time units. In some embodiments, a VSRD can comprise a plurality of sensors including but not limited to an accelerometer, gyros, compass, temperature sensors, proximity detectors, and/or the like sensors. For example, in some embodiments of the VSRD, an embedded accelerometer can be employed to determine the time when a human or animal remains inactive, such a moment can be used to take a scheduled RF-based measurement, gaining accuracy and reliability of the collected sample. In some embodiments, the RF measurements may be made while the subject is on a state of motion, and the obtained measurements may be conditioned or calibrated based on the indication of the accelerometer on whether the subject was active or inactive. In some embodiments, measurements may be taken only when the accelerometer indicates the subject's mobility state is below some threshold (e.g., if the person's velocity is below five miles an hour). Additionally, determining inactive states via an accelerometer and/or the like sensors before collecting an RF-based measurement sample can reduce the amount of energy consumed by the device because an RF sampling device coupled to an accelerometer can consume less energy than an RF device by itself when it is compared to the expended energy utilized on retaking defective samples. Further details with regard to the computation of vital signs can be found with respect to FIG. 7 an example method performed by the VSRD process to calculate a subject's heart rate. Continuing with FIG. 1, after the data received from the monitoring packets e.g., 105 are processed the calculated vital signs can be sent wirelessly to a smart phone e.g., 103 and/or to a computer station e.g., 102. In some embodiments, the sensor 112 determines the vital signs by analyzing the data or RF measurements collected by the sensor itself.

In some embodiments, the monitoring packet 105 can be sent to a smart phone 103 which can compute the requested signs from the gathered RF measurements. The smart phone 103 can then send a vital sign response with the requested measurements to another computer station e.g., 102. In other embodiments sensor telemetry is collected by wireless radios spread around the measurement premises (such as a livestock farm). For example, RF measurements from RF sensors and/or dielectrometers mounted on livestock can be transmitted to a standalone server directly or via a network distributed over the livestock farm. In any case, the telemetry information can be collected into one or more servers and can be accessed directly or via the internet (e.g. using a smartphone).

Figure 2:
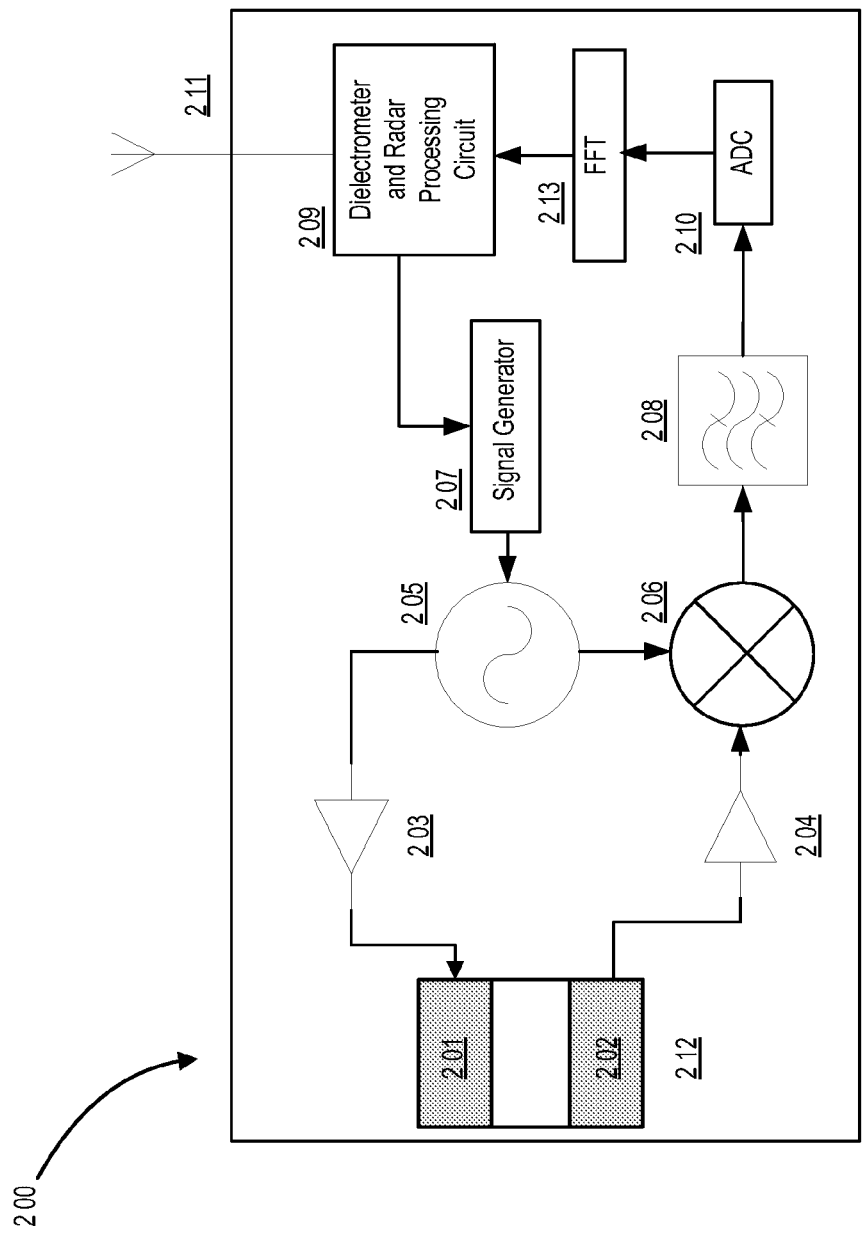
FIG. 2 shows an example of the electrical components comprised in one embodiment of the VSRD sensor.

FIG. 2 shows an example of the electrical components comprised in one embodiment of the VSRD sensor. In some embodiments, an oscillator 205 produces a high frequency microwave signal, for example, a signal between about 200 MHZ and about 3 GHz modulated by, or simply mixed with the signal generator 207. The signal produced by the oscillator 205 may be amplified by the amplifier 203 and then is transmitted to a subject's tissue through an electrode, conductor, or antenna e.g., 201 of a dielectrometric probe and/or radar, e.g., 212. In some embodiments, the VSRD sensor can be implemented comprising a bistatic radar, where the radar includes a transmitter and a receiver located separately, and/or a monostatic radar, where the transmitter and the receiver are collocated. Thereafter, the signal can be propagated to a tissue, and reflected back to the sensor in a plurality of modified signals wherein each signal from said plurality of modified reflected signals corresponds to an intersected member within the tissue. For example, the signal may have been reflected from arteries (e.g. anterior tibial, popliteal, brachial, carotid, etc.), muscles, etc.

In some embodiments, the plurality of reflected signals is received by an electrode or a conductor, e.g., 202 (which may be different than the first electrode 201) of the dielectrometric probe e.g., 212. This plurality of signals is changed in amplitude and/or phase, with respect to the transmitted signals and can be mixed with the original transmitted signal as outputted by the oscillator 205 to obtain an intermediate frequency signal or a beat frequency which reflects signal change; this signal can be further filtered by the band pass filter 208 to discern the signal that will be used to determine the dielectric properties of the targeted tissue, i.e., the artery. For example, the signal may be low-pass filtered to remove noise artifacts. The discerned signal may then be input into an analogue to digital converter, e.g., 210 which samples the signal at a determined rate. Alternatively, some or all of the filtration can be performed digitally. The sampled digital signal may then be input into a fast Fourier transform circuit, e.g., 213, to be further processed by the dielectrometer and radar processing circuit which determines the dielectric properties of the target tissue. These dielectric properties can be transmitted wirelessly to a computer via the antenna 211 to be further processed into vital signs statistics so they can be viewed by a patient, physician and or other interested subjects. Alternatively, in some embodiments, the sensor's electrode, conductor, or antenna e.g., 201 can also be utilized to transmit the aforementioned telemetry signals.

In some embodiments, when the VSRD sensor does not include a dielectrometric probe, in such embodiments, the signals transmitted and received by the radar are sufficient to calculate a human or animal heart rate, respiration rate and blood pressure by the methods and apparatuses presented in this disclosure. In some instances, if a temperature sensor is included in the VSRD sensor, a body temperature of the subject may also be determined (e.g., calculated, estimated or derived) by the noted apparatuses and methods.

Figure 3:
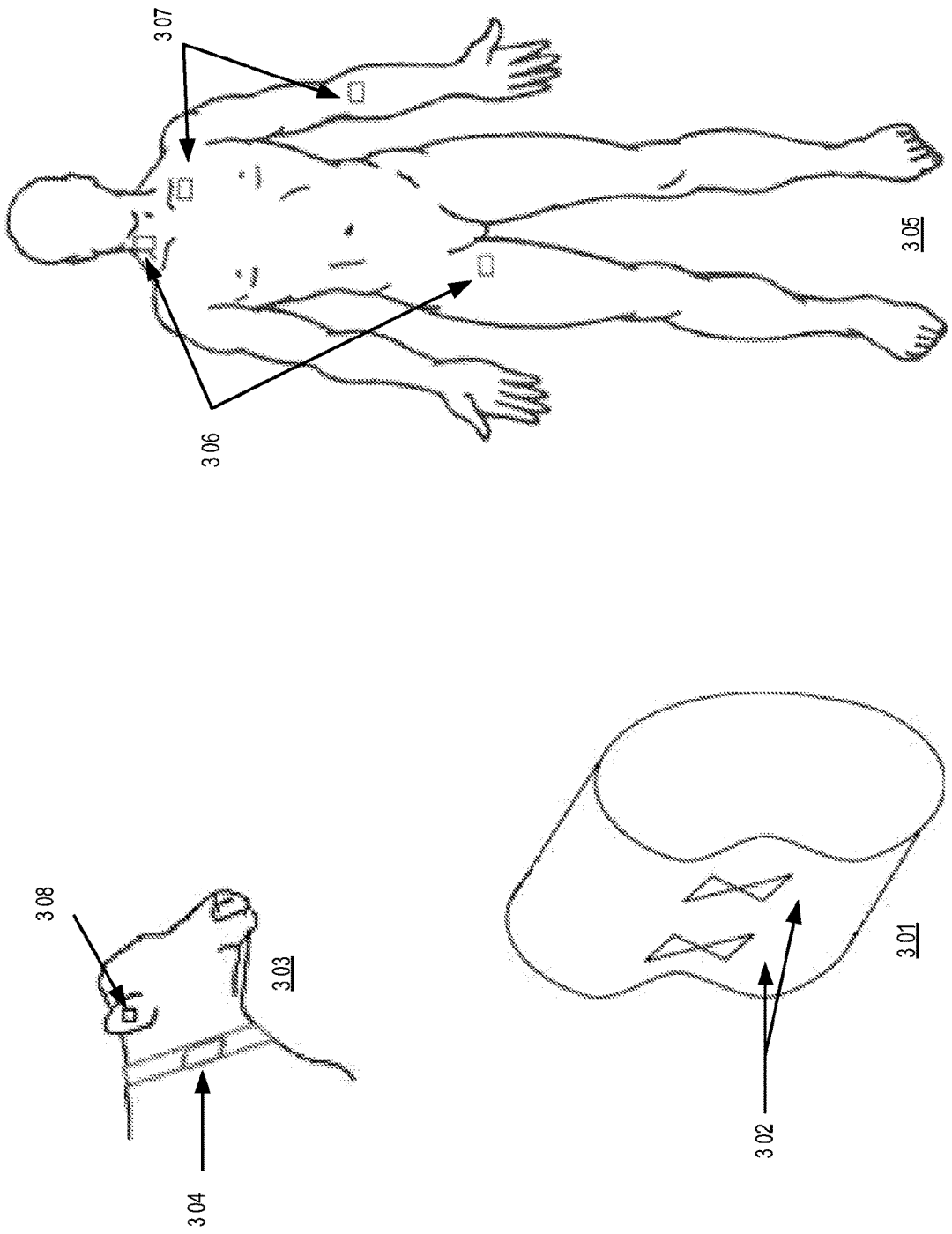
FIG. 3 shows example embodiments of the VSRD sensors, a human and an animal subject wearing the sensor.

FIG. 3 shows various example embodiments of VSRD sensors, a human and an animal subject wearing the sensor. Reference 301 shows an example of the sensor housing, the housing has two antennae, electrodes or conductors 302 which are in direct contact with the subject's skin, fur or clothing to transmit and receive microwave signals.

In another embodiment, the sensor housing can be enhanced with a strap, e.g., 304 to be attached to an animal's neck, e.g., 303 to monitor the animal's vital signs. Moreover, in some embodiments, the VSRD can determine when an animal is regurgitating based on signals collected from the movements of the animal neck's muscles.

Alternatively, in some embodiments, the VSRD sensor can be secured to an animal's ear and/or limb e.g., 308. Moreover, in some embodiments the secured VSRD sensor can be implemented comprising a bistatic radar i.e., a radar with a transmitter and a receiver on each side of the ear or limb and/or comprising a monostatic radar i.e., a radar with a transmitter and a receiver collocated on the same side of the ear or limb. In other further embodiments, a preexisting collar tag and/or a preexisting housing can be utilized to mount or attached the VSRD.

FIG. 3 shows a human body 305 that has a plurality of sensors in direct contact with the skin in proximity with various arteries, e.g., 306 and 307 corresponding to some embodiments of the VSRD. Such sensors can be attached to the human skin by enhancing the sensors with patches with skin friendly adhesives. In some embodiments, a variety of methods including skin patches (with or without adhesives), straps (chest straps, vests, etc.), wrist straps, tags, and/or the like can be used to mount or couple the sensors to the subject. In some embodiments, the mounting may be strategic in that the sensors may be mounted in the vicinity of the tissue being monitored or investigated by the sensors. For example, for respiration measurements, the sensors may be mounted on the torso of the subject. For muscle movement detections, the sensors may be mounted on the neck an animal, and/or the like.

Figure 4:
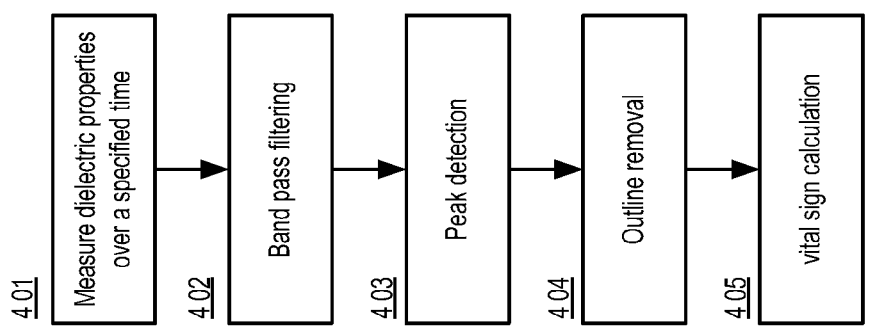
FIG. 4 shows an example method to perform a heart rate calculation in one embodiment of the VSRD system.

FIG. 4 shows an example method to perform a vital sign calculation in one embodiment of the VSRD system, for example, heart or respiration rate. In one embodiment, the VSRD sensor samples a plurality of continuous or stepped wave signals over a period of time reflected from a tissue in a human or animal subject, e.g., 401. Such signals comprise or carry dielectric properties. In some embodiments, the sampled signals are filtered to retain only the signal or signals at a particular frequency or frequency range 402. For example, the signal may be filtered to focus on the frequency range of human or animal respiration if the calculation is for respiration rate, on the frequency range of heart beatings if the calculation is for heart rate, etc., e.g., 404. Further the signal may be filtered to remove noise, for example, the signal may be low-pass filtered. Thereafter, the filtered signal or signals are further processed to determine a peak value, that is, the maximum instantaneous value of the continuous waveform during the sampled time 403. Subsequently the signal is processed to determine how frequently a peak value emerges from the continuous wave signal 304 and then the heart or respiration rate can be calculated 405.

Figure 5A:
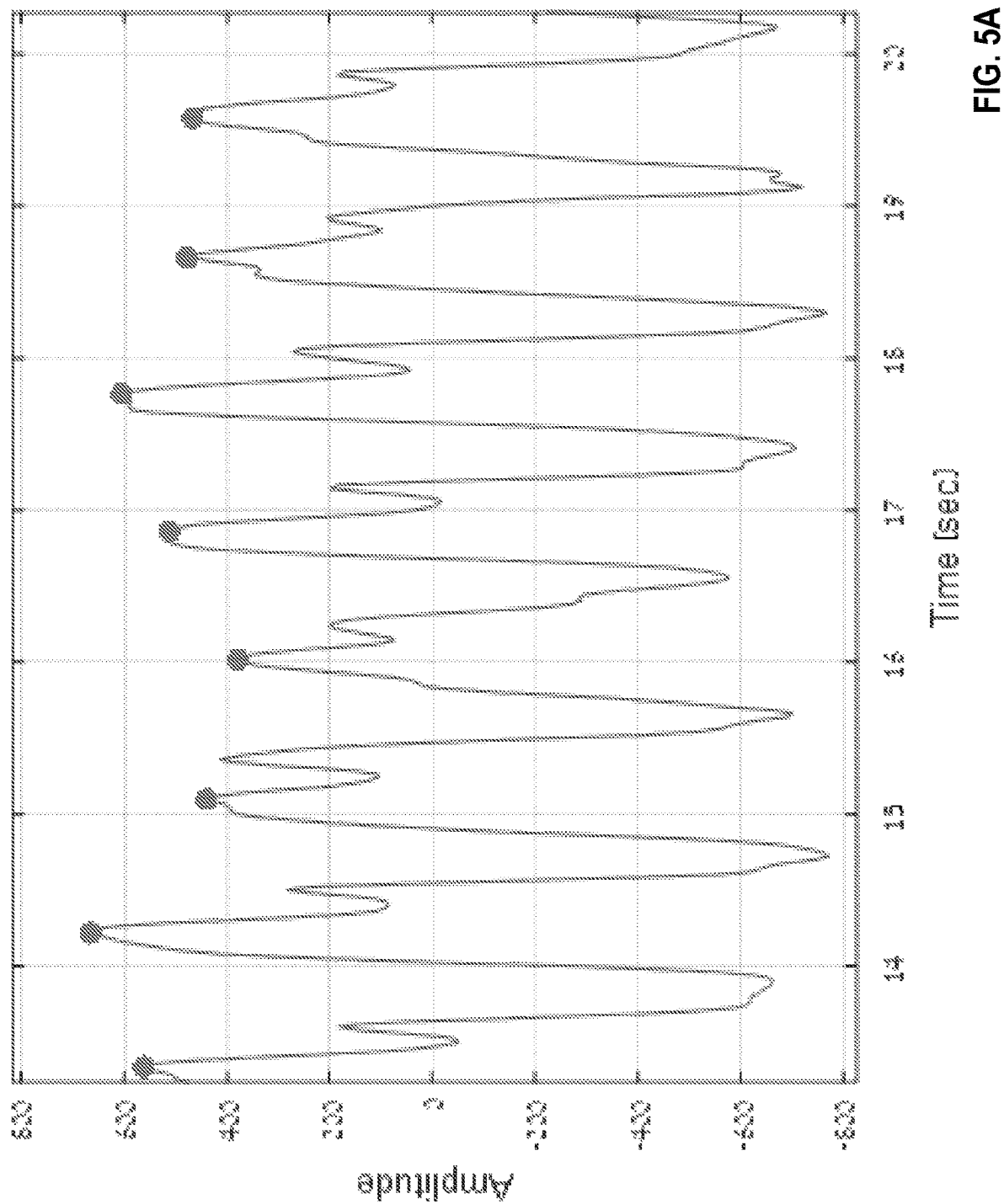
FIGS. 5A-B show example heart rate measurements of a subject taken with the VSRD sensor, in one embodiment of the VSRD system.

FIG. 5 shows examples of heart rate measurements taken with the VSRD. With reference to FIG. 5A, in some embodiments, the depth of a prominent artery along the signal propagation path within the subject is estimated, and the signal reflections corresponding to the estimated depth are utilized to determine the heart rate. The gathered signal reflection is filtered, e.g., low pass filtered, to remove noise artifacts, which may reveal peaks in the signal. In such embodiments, the detection of the prominent peak in the frequency range of the vital sign one is interested in determining (e.g., respiration frequency, heart rate range, etc.) allows one to estimate the rate of the prominent peaks, and hence the periodicity of the occurrence of the peaks. In other words, from the rate of the prominent peaks, one may determine the rate being measured (e.g., the heart rate).

Figure 5B:
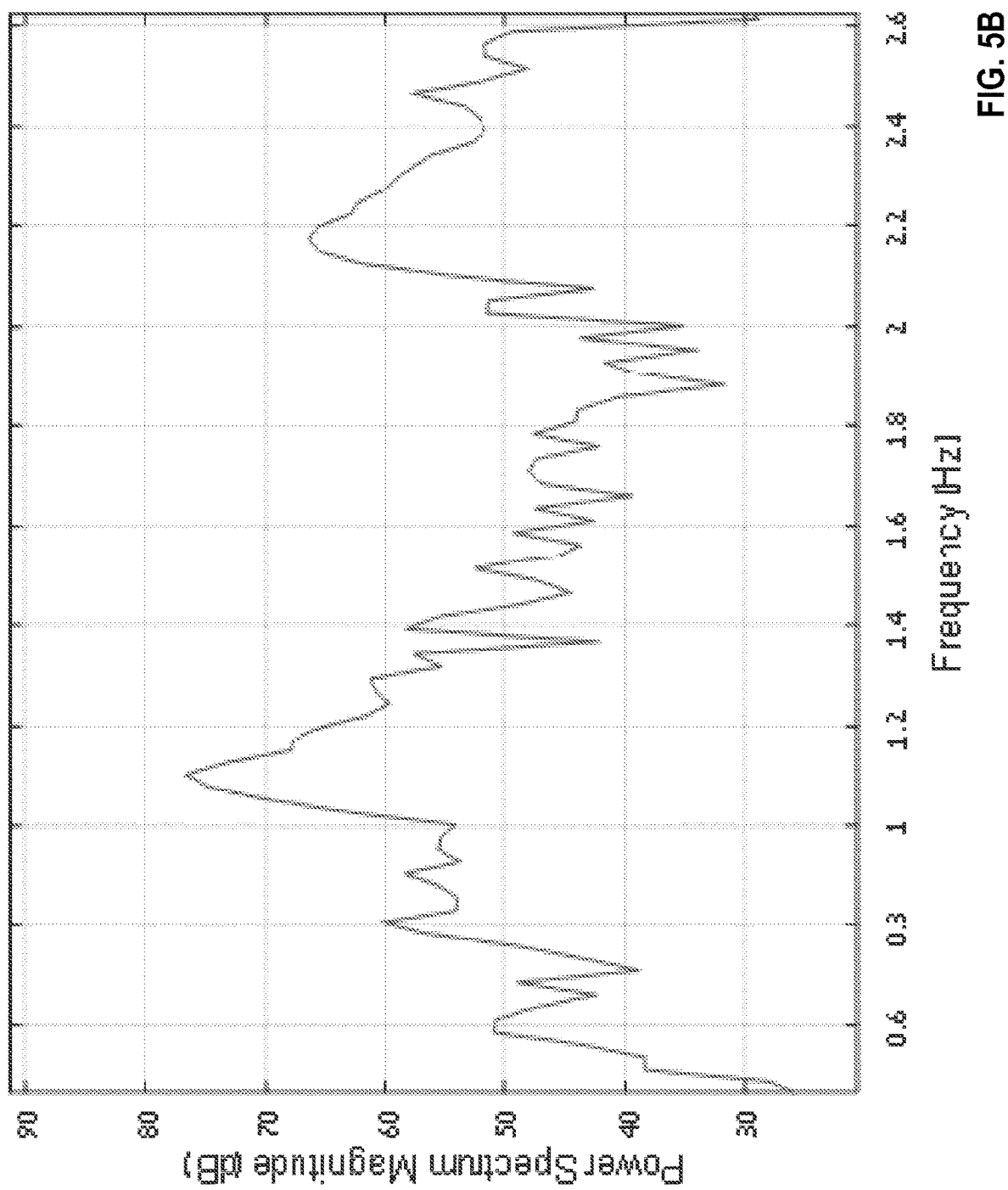

With reference to FIG. 5B, in some embodiments, the PSD of the signal may be calculated and peaks may be detected in the frequency range being considered. In some embodiments, the frequency of the prominent peak may be related to the frequency of the rate being monitored. For example, for a heart rate measurement, one may consider frequency range from about 0.5 Hz to about 3.5 Hz to be the relevant frequency range and the frequency of the most prominent peak appearing in this range may be considered as the frequency of the heart rate.

Figure 6:
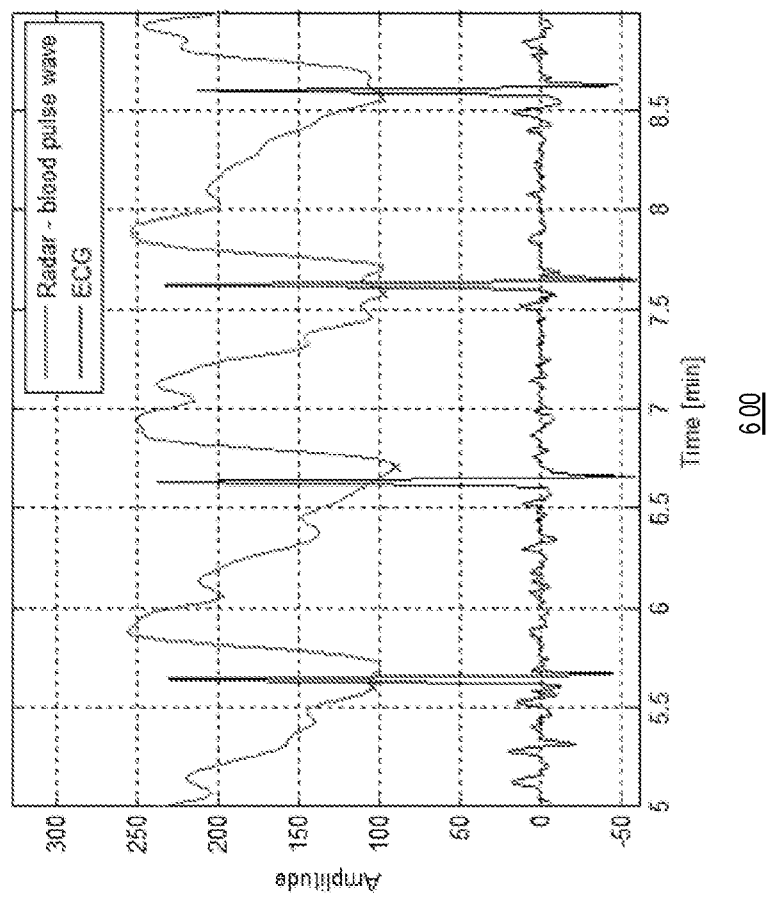
FIG. 6 shows examples of measurements taken with the VSRD sensor: blood pulse wave (shown next to an electrocardiogram for reference), in one embodiment of the VSRD system.

FIG. 6 shows examples of measurements taken with the VSRD system: blood pulse wave (shown next to an electrocardiogram for reference) in one embodiment of the VSRD. In some embodiments, heart rate sensor measurements can be obtained by utilizing the sensor's embedded radar by positioning the sensor in proximity to a subject's artery. The heart rate can be measured from received radio frequency signals that have been reflected from their intersection with the subject's artery. Similarly, the sensor can calculate the respiration rate from the sensor signals by collecting the reflected signals received by the sensor, and detecting the principal frequency corresponding to the respiratory rate as described above.

Figure 7:
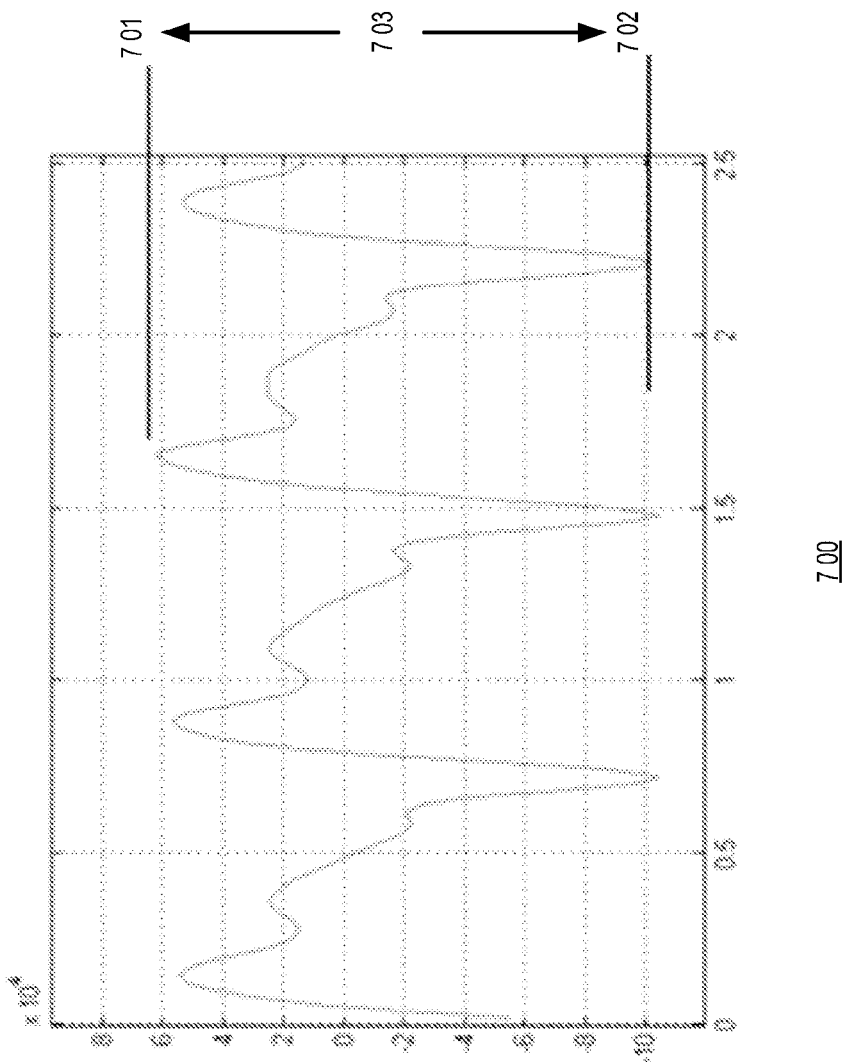
FIG. 7 shows an example method to calculate pulse pressure based on systolic and diastolic blood pressure points, in one embodiment of the VSRD system.

FIG. 7 shows an example signal obtained by the VSRD sensor showing the pulse pressure based on systolic and diastolic blood pressure points, in one embodiment of the VSRD. In some embodiments, the subject's blood pressure can be obtained from the signal reflected from the subject's artery, e.g., 700. The amplitude of the signal waveform can be calibrated by utilizing a blood measurement device that serves as a reference blood pressure meter. Thereafter, the systolic blood pressure can be determined as a function of the maximum point of the calibrated pulse waveform, e.g., 701. Similarly, the diastolic blood pressure can be determined as a function of the minimum point of the calibrated pulse waveform e.g., 702. The difference between the maximum and the minimum points of the calibrated pulse waveform can correspond to the subject's pulse pressure. In some alternative embodiments, the time difference between peaks of pulse pressure waveforms, or equivalently the frequency of a transformed signal (e.g., FFT-transformed) can be utilized to assess the systolic and diastolic blood pressure.

In some embodiments of the VSRD, the RF signals employed to calculate measurements can comprise signals reflected from muscles in addition or alternatively to not signals reflected from an artery. For example, signals reflected from specific muscles within a tissue may be analyzed to determine when a human or animal is chewing. Such muscle signals are reflected from a different depth than the arteries and thus, they can be processed utilizing the methods and devices as described herein by adapting the corresponding signal frequencies. For example, an estimate of the depth of the muscle and isolation of the signals reflected from such muscle (based on frequency shifts, for example) allows one to identify the reflected signals with the muscles and apply the systems and methods disclosed herein to determine the desired properties of the muscle.

Figure 8:
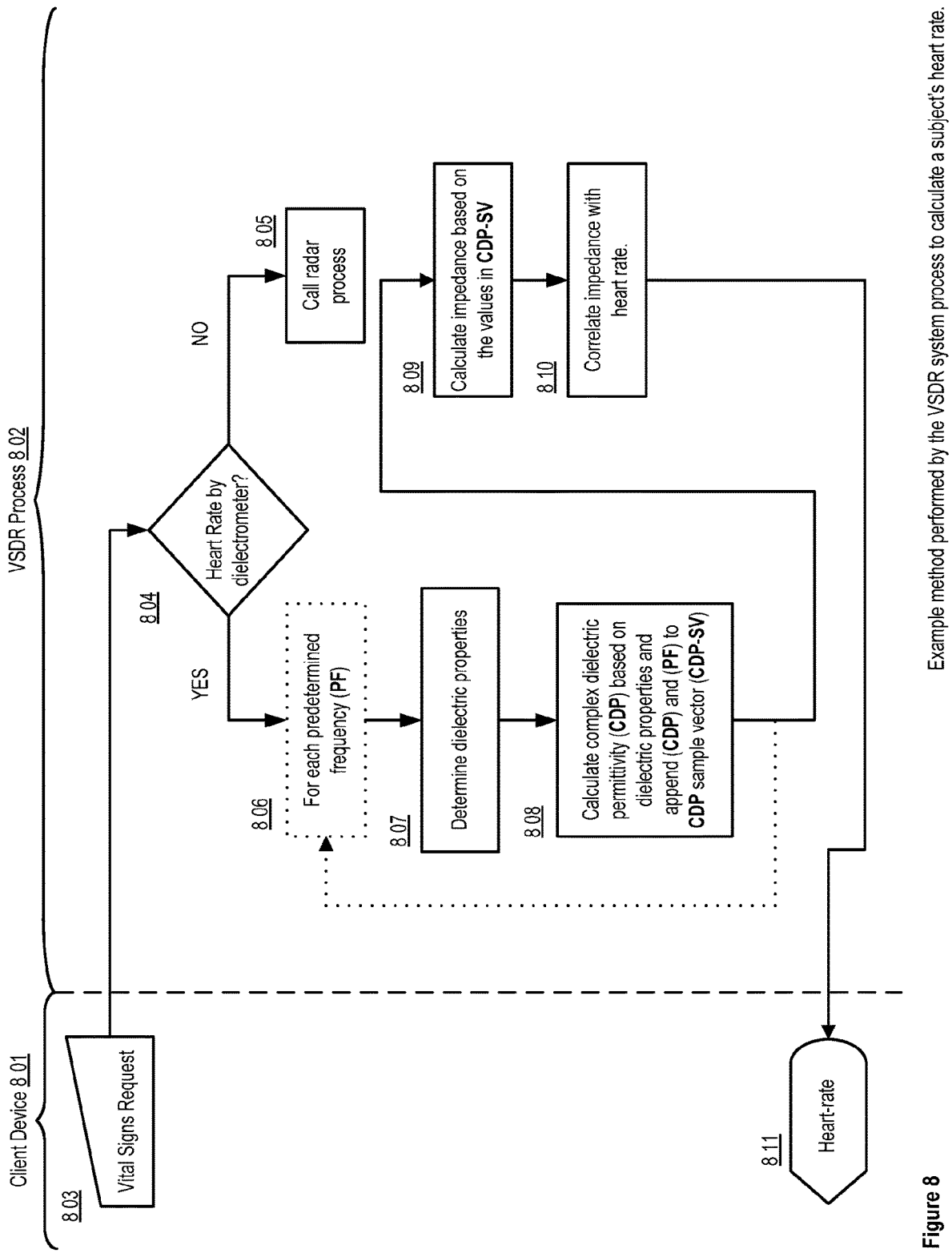
FIG. 8 an example method performed by the VSRD process to calculate a subject's heart rate, in one embodiment of the VSRD system.

FIG. 8 shows an example method performed by the VSRD process to calculate a subject's heart rate, in one embodiment of the VSRD system. In one embodiment, a client device 801 sends a request of vital signs 803 to the VSRD process 802. Thereafter, the VSRD process evaluates if the request includes a request of heart-rate dielectrometer based measurement e.g., 804. If the request does not include a request of heart-rate dielectrometer based measurement then, the process can proceed to check for other requested vital signs based on radar measurements e.g., 805. If however, the request includes a heart-rate dielectrometer based measurement then the VSRD process enters a loop wherein for each of a frequency (PF) in a predetermined set of frequencies e.g., 806, the process determines dielectric properties of a tissue and calculates a complex dielectric permittivity (CDP) of the tissue based on the tissue's dielectric properties and can append the calculated (CDP) and (PF) to a CDP sample vector (CDP-SV) containing the complex dielectric permittivity of each predetermined frequency PF in the aforementioned set. Thereafter, an impedance value is calculated based on the values contained in the CDP sample vector (CDP-SV) e.g., 809 to correlate the impedance with a heart-rate value e.g., 810 and further send the calculated rate to the client device. In some embodiments, the CDP-SV is sampled over time allowing for the creation of a time-varying signal that can be used for determining a heart rate value. For example, the heart rate can be derived from or estimated based on the variations in time of the sampled CDP signal (e.g., frequency of at least substantially periodic variation that occurs in the frequency range relevant to heart rates).

Communication between various components, including a processor which includes computer instructions operable thereon which are configured to at least one of control the disclosed devices and systems, and calculate diastolic and systolic values, heart rates, blood pressure, body temperature and respiration rates, as well as calibration of values, can be wired communication, and/or wireless via an analog short range communication mode, or a digital communication mode including, for example, WI-FI or BLUETOOTH®. Additional examples of such communication can include communication across a network. Such a network can include a local area network ("LAN"), a wide area network ("WAN"), or a global network, for example. The network can be part of, and/or can include any suitable networking system, such as the Internet, for example, and/or an Intranet.

Generally, the term "Internet" may refer to the worldwide collection of networks, gateways, routers, and computers that use Transmission Control Protocol/Internet Protocol ("TCP/IP") and/or other packet based protocols to communicate therebetween.

In some embodiments, the disclosed systems and devices may comprise one or more transmission elements for communication between components thereof. In some embodiments, the transmission element can include at least one of the following: a wireless transponder, or a radio-frequency identification ("RFID") device. The transmission element can include at least one of the following, for example: a transmitter, a transponder, an antenna, a transducer, and/or an RLC circuit or any suitable components for detecting, processing, storing and/or transmitting a signal, such as electrical circuitry, an analog-to digital ("A/D") converter, and/or an electrical circuit for analog or digital short range communication.

In some embodiments, a controller/processor according to some embodiments and/or any other relevant component of disclosed devices and systems can include a memory, a storage device, and an input/output device. Various implementations of some of embodiments disclosed, in particular at least some of the processes discussed (or portions thereof), may be realized in digital electronic circuitry, integrated circuitry, specially configured ASICs (application specific integrated circuits), computer hardware, firmware, software, and/or combinations thereof (e.g., the disclosed processor/controllers). These various implementations, such as associated with the disclosed devices/systems and the components thereof, for example, may include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

Such computer programs (also known as programs, software, software applications or code) include machine instructions/code for a programmable processor, for example, and may be implemented in a high-level procedural and/or object-oriented programming language, and/or in assembly/machine language. As used herein, the term "machine-readable medium" refers to any computer program product, apparatus and/or device (e.g., nontransitory mediums including, for example, magnetic discs, optical disks, flash memory, Programmable Logic Devices (PLDs)) used to provide machine instructions and/or data to a programmable controller/processor, including a machine-readable medium that receives machine instructions as a machine-readable signal. The term "machine-readable signal" refers to any signal used to provide machine instructions and/or data to a programmable processor.

To provide for interaction with a user, the subject matter described herein may be implemented on a computing device which includes a display device (e.g., a LCD (liquid crystal display) monitor and the like) for displaying information to the user and a keyboard and/or a pointing device (e.g., a mouse or a trackball, touchscreen) by which the user may provide input to the computer. For example, this program can be stored, executed and operated by the dispensing unit, remote control, PC, laptop, smartphone, media player or personal data assistant ("PDA"). Other kinds of devices may be used to provide for interaction with a user as well.

For example, feedback provided to the user may be any form of sensory feedback (e.g., visual feedback, auditory feedback, or tactile feedback), and input from the user may be received in any form, including acoustic, speech, or tactile input. Certain embodiments of the subject matter described herein may be implemented on a computing system and/or devices that includes a back-end component (e.g., as a data server), or that includes a middleware component (e.g., an application server), or that includes a front-end component (e.g., a client computer having a graphical user interface or a Web browser through which a user may interact with an implementation of the subject matter described herein), or any combination of such back-end, middleware, or front-end components.

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be an example and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure. Still other embodiments of the present disclosure are patentable over prior art references for expressly lacking one or more features disclosed in the prior art (i.e., claims covering such embodiments may include negative limitations).

Any and all references to publications or other documents, including but not limited to, patents, patent applications, articles, webpages, books, etc., presented anywhere in the present application, are herein incorporated by reference in their entirety. One or more features and/or embodiments disclosed in one or more of incorporated by reference documents herein can also be combined with one or more features/embodiments of the present disclosure to yield yet further embodiments (of the present disclosure).

Moreover, all definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is currently claimed is:

1. A vital sign measuring apparatus, comprising:
one or more RF sensors configured to be arranged external to a subject and on or adjacent the skin of the subject at a first location proximate to one or more arteries of the subject;
an external dielectrometer probe configured to be arranged external to the subject and on or adjacent the skin of the subject proximate to one or more arteries of the subject;
circuitry for the probe and the one or more RF sensors configured to:
generate one or more first radio-frequency (RF) waves for transmission towards the one or more arteries,
transmit the one or more first radio-frequency (RF) waves towards the one or more arteries of the subject,
receive one or more reflected RF waves therefrom, and
receive one or more dielectrometer probe signals from the external dielectrometer probe;
and
a processor communicably coupled to the circuitry and having computer instructions operating thereon configured to cause the processor to:
receive one or more requests for one or more vital signs of the subject,
determine if the one or more requests comprises a request for heart-rate measurement of the subject, or a request for at least one of blood pressure and respiration rate of the subject,
process at least one of the one or more dielectrometer signals and the one or more reflected RF waves,
determine the heart-rate measurement based on the processed one or more dielectrometer signals upon the one or more requests comprising the request for heart-rate measurement of the subject, and determine the at least one of blood pressure and respiration rate based on the processed one or more reflected RF waves upon the one or more requests comprising the request for at least one of blood pressure and respiration rate of the subject.

2. The apparatus of claim 1, wherein the one or more RF sensors comprise a monostatic radar.

3. The apparatus of claim 1, wherein the one or more RF sensors comprise a bistatic radar.

4. The apparatus of claim 1, wherein the apparatus is configured with flexibility for conforming the apparatus to the skin of the subject.

5. The apparatus of claim 1, wherein the one or more RF sensors are configured to be are placed on or adjacent to the skin of the subject via a wearable device, a wearable garment, or an adhesive.

6. The apparatus of claim 5, wherein the wearable garment comprises one or more of an article of clothing, a collar, a wrist strap, an ear tag, and a skin patch.

7. The apparatus of claim 1, wherein the dielectrometer probe is configured to be placed on or adjacent to the skin of the subject via a wearable device, a garment, or an adhesive.

8. The apparatus of claim 1, wherein the transmitted RF waves range from 200 MHz to 3 GHz.

9. The apparatus of claim 1, wherein the computer instructions are further configured to cause the processor to resolve the received reflected RF waves according to one or more depths into the subject from which one or more of the reflected RF waves occurred.

10. The apparatus of claim 1, wherein the computer instructions are further configured to cause the processor to condition the received, reflected RF waves using band pass filtering.

11. The apparatus of claim 1, wherein a frequency range for the one or more reflected RF waves corresponds between 0.5 Hz to 2.5 Hz.

12. The apparatus of claim 1, wherein the computer instructions are further configured to cause the processor to identify a prominent peak frequency in a frequency range of the received, reflected RF waves corresponding to respirations of the subject from a fast Fourier transform of the one or more received reflected RF waves.

13. The apparatus of claim 12, wherein the frequency range is between 0.1 Hz to 1 Hz.

14. The apparatus of claim 13, wherein the computer instructions are further configured to cause the processor to determine the respiration rate of the subject as a function of the peak frequency.

15. The apparatus of claim 1, wherein the computer instructions are further configured to cause the processor to:
calibrate at least one amplitude of a pulse waveform based on the one or more received reflected RF waves with respect to a reference blood pressure measurement; and
calculate a difference between a maximum of the calibrated amplitude representing systolic blood pressure and a minimum of the calibrated amplitude representing diastolic blood pressure.

16. The apparatus of claim 1, wherein the computer instructions are further configured to cause the processor to determine a complex permittivity from the one or more dielectrometer probe signals.

17. The apparatus of claim 16, wherein the computer instructions are further configured to cause the processor to determine one or more changes in radar characteristics of the reflected RF waves.

18. The apparatus of claim 17, wherein the computer instructions are further configured to cause the processor to determine other vital signs based on the one or more changes in the radar characteristics of the reflected RF waves.

* * * * *